United States Patent
Kuwabara

(10) Patent No.: US 6,703,959 B2
(45) Date of Patent: Mar. 9, 2004

(54) SIGNAL DETECTING METHOD AND SIGNAL DETECTING DEVICE

(75) Inventor: Takao Kuwabara, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 10/230,165

(22) Filed: Aug. 29, 2002

(65) Prior Publication Data

US 2003/0043064 A1 Mar. 6, 2003

(30) Foreign Application Priority Data

Aug. 31, 2001 (JP) ....................................... 2001-263285
May 10, 2002 (JP) ....................................... 2002-134944

(51) Int. Cl.[7] ............................ H03M 1/12; H05G 1/64
(52) U.S. Cl. ...................... 341/155; 341/122; 341/143; 378/98.7; 378/98.8
(58) Field of Search .................................. 341/155, 118, 341/120, 144; 378/98.7, 98.8, 108

(56) References Cited

U.S. PATENT DOCUMENTS

| | | | | | |
|---|---|---|---|---|---|
| 5,724,037 A | * | 3/1998 | Lee | ............................. | 341/143 |
| 5,869,837 A | * | 2/1999 | Huang | ................... | 250/370.09 |
| 5,877,715 A | * | 3/1999 | Gowda et al. | ............... | 341/122 |
| 5,886,659 A | * | 3/1999 | Pain et al. | .................. | 341/155 |
| 5,920,274 A | * | 7/1999 | Gowda et al. | ............... | 341/155 |
| 5,982,318 A | * | 11/1999 | Yiannoulos | .................. | 341/155 |
| 6,163,029 A | * | 12/2000 | Yamada et al. | ......... | 250/370.09 |
| 6,166,367 A | * | 12/2000 | Cho | .......................... | 250/208.1 |
| 6,243,441 B1 | * | 6/2001 | Zur | ............................. | 378/98.8 |
| 6,404,851 B1 | * | 6/2002 | Possin et al. | .............. | 378/98.7 |
| 6,545,624 B2 | * | 4/2003 | Lee et al. | .................... | 341/155 |
| 6,628,436 B1 | * | 9/2003 | Sone | .......................... | 358/505 |

* cited by examiner

Primary Examiner—Michael Tokar
Assistant Examiner—Linh V Nguyen
(74) Attorney, Agent, or Firm—Sughrue Mion, PLLC

(57) ABSTRACT

In a signal detecting method of repeating the processes of initiating accumulation of charge signals by switching an integrating amplifier to an accumulator mode, retaining a first electric signal outputted from the integrating amplifier immediately after switching to the accumulator mode, finding a difference as a signal component between a second electric signal outputted from the integrating amplifier immediately before switching to a reset mode after completing accumulation of the charge signals and the first electric signal, and converting and outputting the signal component into a digital signal. Here, the signal component concerning a first charge signal is retained by second signal retaining means and then converted into the digital signal. Further, the integrating amplifier is switched to the accumulator mode after completing accumulation concerning the first charge signal but before completing conversion into the digital signal to initiate accumulation concerning a second charge signal.

9 Claims, 12 Drawing Sheets

FIG.1A
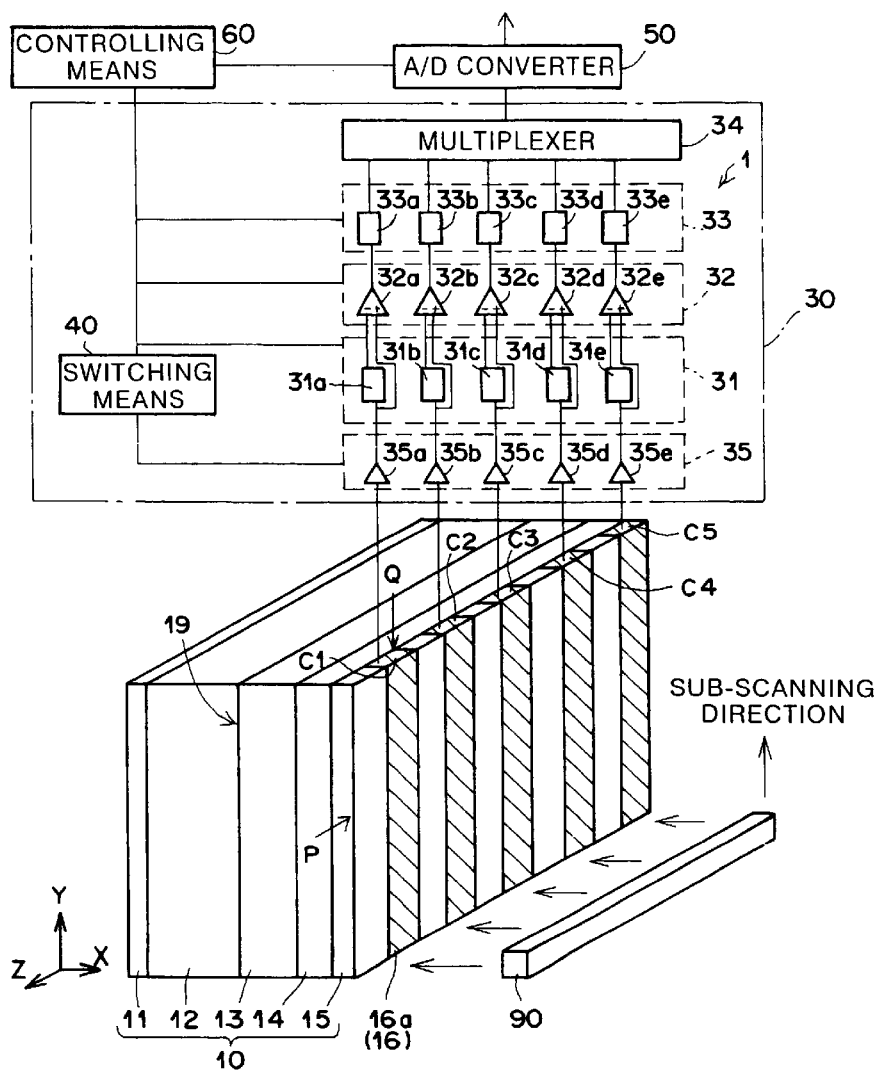
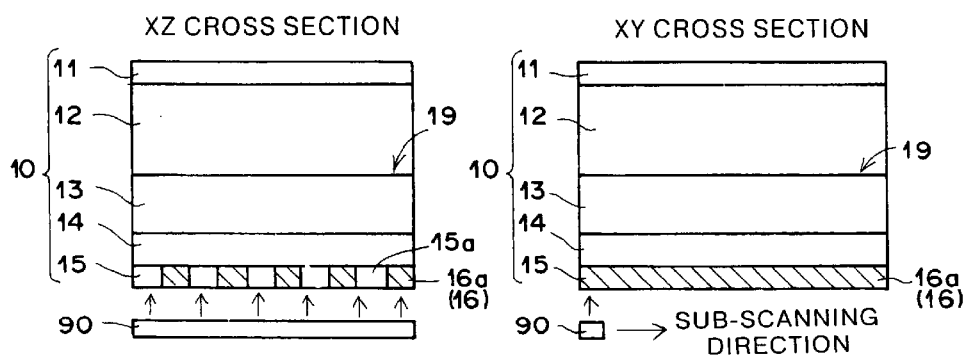
FIG.1B  FIG.1C

SIGNAL DETECTING METHOD AND SIGNAL DETECTING DEVICE

BACKGROUND OF THE INVENTION

1. Field of the Invention

The present invention relates to a signal detecting method and a signal detecting device using an integrating amplifier for detecting charge signals by correlated double sampling.

2. Description of the Related Art

Conventionally, image information retrieving apparatuses, which retrieve image information by use of photoelectric converter elements such as CCD's or photomultipliers or solid state image detectors, have been utilized in various fields.

Particularly in the field of medical science, there has been disclosed a solid state radiation image detector capable of recording radiation image information on an electric accumulator as an electrostatic latent image by means of accumulating electric charges in an amount corresponding to a dosage of X-rays irradiated with a radiation image capturing apparatus or the like as electric charges for a latent image, and capable of retrieving the radiation image information by scanning with a laser beam or a line light source as retrieving light.

Moreover, in the above-mentioned image information retrieving apparatus, radiation image capturing apparatus and the like, integrating amplifiers are generally used for detecting retrieved image signals because the integrating amplifiers are processible into integrated circuits and generate a relatively small amount of noise. Such an integrating amplifier is designed to initiate accumulation of electric charges when switched to an accumulator mode, to discharge the accumulated electric charges when switched to a reset mode and thereby to output electric signals corresponding to the amount of the electric charges.

Here, immediately after the integrating amplifier is switched to the accumulator mode, an offset called a charge feedthrough attributable to capacitance of a switch inside the integrating amplifier is outputted as shown in FIG. 8. The charge feedthrough is not always constant but is fluctuant; therefore, it is not possible to obtain accurate signal components corresponding to the image information if processing is applied that subtracts an uniform offset. In this context, processing called correlated double sampling is applied in order to eliminate the influence of charge feedthrough. Correlated double sampling refers to processing, which can eliminate the influence of the charge feedthrough by means of measuring a difference between an electric signal to be outputted immediately after the integrating amplifier is switched to the accumulator mode and an electric signal to be outputted immediately before the integrating amplifier is switched to the reset mode, and by defining the difference as a signal component.

Now, there are two methods of correlated double sampling, namely, analog correlated double sampling (ACDS) and digital correlated double sampling (DCDS).

The analog correlated double sampling uses a readout circuit as illustrated in FIG. 9 and is operated under control corresponding to a timing chart as shown in FIG. 10. The readout circuit includes an integrating amplifier 1, first signal retaining means 2 for retaining an electric signal to be outputted immediately after switching to an accumulator mode, second signal retaining means 3 for retaining an electric signal to be outputted immediately before switching to a reset mode, a differentiator circuit 4 for finding a difference between the electric signals retained in the first signal retaining means 2 and in the second signal retaining means 3 and for outputting the difference as a signal component, and an A/D converter 5 for converting the signal component into a digital signal.

As shown in FIG. 10, a first electric signal to be outputted immediately after the integrating amplifier 1 is switched to the accumulator mode is retained by the first signal retaining means 2 first, and after passage of a sufficient time period for accumulating electric charges in the integrating amplifier 1, a second electric signal to be outputted immediately before the integrating amplifier 1 is switched to the reset mode is retained by the second signal retaining means 3. Then, the difference between the first electric signal and the second electric signal is determined as the signal component with the differentiator circuit 4 and the signal component is converted and outputted by the A/D converter 5. Note that the timing chart illustrated in FIG. 10 shows the control timing for detecting signals for each pixel.

Meanwhile, the digital correlated double sampling uses a readout circuit as illustrated in FIG. 11 and is operated under control corresponding to a timing chart as shown in FIG. 12. The readout circuit includes an integrating amplifier 6, signal retaining means 7 for retaining a first electric signal to be outputted immediately after switching to an accumulator mode and a second electric signal to be outputted immediately before switching to a reset mode, and an A/D converter 8 for converting the signals retained by the signal retaining means 7 into digital signals.

As shown in FIG. 12, the first electric signal to be outputted immediately after the integrating amplifier 6 is switched to the accumulator mode is retained by the signal retaining means 7 first, and the retained first electric signal is outputted by the A/D converter 8 as a first digital signal. Then, after passage of a sufficient time period for accumulating electric charges, the second electric signal to be outputted immediately before the integrating amplifier 1 is switched to the reset mode is retained by the signal retaining means 7. Thereafter, the retained second electric signal is converted into a second digital signal and outputted by the A/D converter 8. Note that a difference between the first digital signal and the second digital signal is computed by software loaded on an image processing apparatus or the like to be connected subsequent to the A/D converter 8.

However, the analog correlated double sampling has the following problem. Specifically, when radiation image information is read out of the radiation image detector while accumulating the electric charge one-on-one for each pixel in the integrating amplifier, for example, the first signal retaining means 2 and the second signal retaining means 3 must retain the first electric signal and the second electric signal during digitalization of the signal component by the A/D converter 5. Accordingly, accumulation of an electric charge corresponding to a subsequent pixel cannot be initiated before A/D conversion of a first pixel is completed. Therefore, a long processing time period is required for obtaining a digital signal for one pixel, because the required time period combines a time period for accumulating the electric charge and a time period for A/D conversion.

Similarly, the digital correlated double sampling has the following problem. When the radiation image information is read out of the radiation image detector while accumulating the electric charge one-on-one for each pixel in the integrating amplifier, for example, the signal retaining means 7 must retain the second electric signal until digitalization of the second electric signal is completed. Accordingly, accumulation of an electric charge corresponding to a subsequent pixel cannot be initiated beforehand. Therefore, a long processing time period is required for obtaining a digital signal for one pixel as similar to the above-described case with the analog correlated double sampling, as the required time period combines a time period for accumulating the electric charge and a time period for A/D conversion.

Moreover, in the case of retrieving the radiation image by scanning the retrieving light as previously described, the time period for accumulating the electric charge needs to be prolonged because speed of response to the retrieving light is slow. Nevertheless, such processing time is preferred to be as short as possible.

Furthermore, in the case of retrieving the radiation image by scanning the retrieving light as described above, it is not possible to retrieve charge signals outputted during A/D conversion. Accordingly, the charge signals during such a period are overlooked, and the S/N ratio of the retrieved radiation image is resultantly deteriorated.

SUMMARY OF THE INVENTION

In consideration of the foregoing problems, it is an object of the present invention to provide a signal detecting method and a signal detecting device capable of shortening process time upon detecting the charge signals read out of the radiation image detector or the like by correlated double sampling using an integrating amplifier, and capable of avoiding occurrence of deterioration in the S/N ratio of the radiation image as described above.

A first signal detecting method of the present invention is a signal detecting method of repeating the processes of initiating accumulation of charge signals by switching an integrating amplifier to an accumulator mode, retaining a first electric signal outputted from the integrating amplifier immediately after the integrating amplifier is switched to the accumulator mode, finding a difference between a second electric signal outputted from the integrating amplifier immediately before the integrating amplifier is switched to a reset mode after completing accumulation of the charge signals and the first electric signal retained by the integrating amplifier to define the difference as a signal component, and converting the signal component into a digital signal and thereby outputting the digital signal. Here, the signal detecting method includes the steps of retaining the signal component obtained in connection with a first charge signal, converting the retained signal component into the digital signal, and switching the integrating amplifier to the accumulator mode after completing accumulation concerning the first charge signal but before completing conversion into the digital signal so as to initiate accumulation concerning a second charge signal.

Here, the first signal detecting method refers to a signal detecting method concerning the so-called analog correlated double sampling as described above.

Moreover, the foregoing "charge signals" refer to signals obtained by converting image information with a photoelectric converter element such as a CCD or a photomultiplier, or signals read out of the solid state radiation image detector, for example.

Moreover, the foregoing expression of "immediately after the integrating amplifier is switched to the accumulator mode" may be defined as a moment simultaneous with a moment of switching to the accumulator mode or a moment after passage of a certain time period after switching to the accumulator mode. However, it is preferred that such a moment takes place after settlement of a charge feedthrough phenomenon, which occurs in the event of switching from the reset mode to the accumulator mode.

Moreover, the foregoing expression of "after completing accumulation of the charge signals" refers to passage of a predetermined accumulation time period of the integrating amplifier.

Moreover, the foregoing expression of "immediately before the integrating amplifier is switched to a reset mode" is preferably set as a moment in advance of time for switching to the reset mode just by a period required for confirmation of the retention.

Moreover, if the charge signals are the signals photoelectrically converted with the CCD, for example, then the foregoing "first charge signal" refers to a charge signal outputted from the CCD in response to a first pixel, and the foregoing "second charge signal" refers to a charge signal outputted subsequently from the CCD in response to a second pixel adjacent to the first pixel. Meanwhile, if the charge signals are the signals retrieved by irradiating linear retrieving light with a line light source onto a solid state radiation image detector, then the "first charge signal" refers to a charge signal retrieved by irradiating the retrieving light onto a first line, and the "second charge signal" refers to a charge signal retrieved subsequently by irradiating the retrieving light onto a second line adjacent to the first line.

A second signal detecting method of the present invention is a signal detecting method of repeating the processes of initiating accumulation of charge signals by switching an integrating amplifier to an accumulator mode, retaining a first electric signal outputted from the integrating amplifier immediately after the integrating amplifier is switched to the accumulator mode by signal retaining means, converting the retained first electric signal into a first digital signal, retaining a second electric signal outputted from the integrating amplifier immediately before the integrating amplifier is switched to a reset mode after completing accumulation of the charge signals, and converting the retained second signal into a second digital signal and thereby outputting the second digital signal. Here, the signal detecting method includes the steps of retaining the first electric signal obtained in connection with a first charge signal by first signal retaining means, retaining the second electric signal obtained in connection with the first charge signal by second signal retaining means, and switching the integrating amplifier to the accumulator mode after completing accumulation concerning the first charge signal but before completing conversion of the second electric signal into the second digital signal so as to initiate accumulation concerning a second charge signal.

Here, the second signal detecting method refers to a signal detecting method concerning the so-called digital correlated double sampling as described above.

Moreover, the foregoing "signal retaining means" refers to a device including a switch and a capacitor, for example, so that the device can retain the electric signals by accumulating electric charges in the capacitor while turning the switch on.

Moreover, the foregoing expression of "after completing accumulation concerning the first charge signal" refers to passage of a predetermined accumulation time period of the integrating amplifier. However, the predetermined accumulation time period of the integrating amplifier is set longer than a time period required for converting the electric signal into the digital signal. In other words, when the accumulation time period concerning the first charge signal has passed, conversion of the first electric signal concerning the first charge signal into the first digital signal is to be completed already.

A third signal detecting method of the present invention is a signal detecting method of repeating the processes of initiating accumulation of charge signals by switching an integrating amplifier to an accumulator mode, retaining a first electric signal outputted from the integrating amplifier immediately after the integrating amplifier is switched to the accumulator mode by signal retaining means, converting the retained first electric signal into a first digital signal by converting means, retaining a second electric signal outputted from the integrating amplifier immediately before the integrating amplifier is switched to a reset mode after completing accumulation of the charge signals by signal retaining means, and converting the retained second electric signal into a second digital signal by the converting means and thereby outputting the second digital signal. Here, the signal detecting method includes the steps of retaining the first electric signal by first signal retaining means, converting the retained first electric signal into a first digital signal by first converting means, retaining the second electric signal by second signal retaining means, converting the retained second electric signal into a second digital signal by second converting means, switching the integrating amplifier to the accumulator mode after completing accumulation concerning the first charge signal but before completing conversion of the retained second electric signal into the second digital signal so as to initiate accumulation concerning a second charge signal, retaining the first electric signal concerning the second charge signal to be outputted from the integrating amplifier immediately after the integrating amplifier is switched to the accumulator mode, and initiating conversion of the first electric signal concerning the second charge signal into the first digital signal before completing conversion of the second electric signal concerning the first charge signal into the second digital signal.

Here, the third signal detecting method refers to the signal detecting method concerning the so-called digital correlated double sampling as similar to the second signal detecting method.

A first signal detecting device of the present invention includes an integrating amplifier for accumulating charge signals and for outputting electric signals corresponding to amounts of the accumulated electric charges, switching means for switching the integrating amplifier between an accumulator mode and a reset mode, first signal retaining means for retaining a first electric signal outputted immediately after the integrating amplifier is switched to the accumulator mode by the switching means, a differentiator circuit for finding a difference between a second electric signal outputted from the integrating amplifier immediately before the integrating amplifier is switched to the reset mode by the switching means and the first electric signal retained by the first signal retaining means and thereby outputting the difference as a signal component, second signal retaining means for retaining the signal component outputted from the differentiator circuit, and converting means for converting the signal component retained by the second signal retaining means into a digital signal.

Here, the first signal detecting device relates to a device for performing the so-called analog correlated sampling. Accordingly, it is preferred that the first signal detecting device conducts signal detection in accordance with the first signal detecting method.

Moreover, in the first signal detecting device, the integrating amplifier, the first signal retaining means, the differentiator circuit and the second signal retaining means may be respectively provided on each of line electrodes of an image detector. Here, the image detector is formed by serially stacking a first electrode layer having transmissivity with respect to an electromagnetic wave for recording, a recording photoconductive layer which takes on conductivity by receiving irradiation of the electromagnetic wave for recording transmitted through the first electrode layer, an electric accumulator for accumulating electric charges generated in the recording photoconductive layer by irradiation of the electromagnetic wave for recording as electric charges for a latent image, a retrieving photoconductive layer which takes on conductivity by receiving irradiation of an electromagnetic wave for retrieval, and a second electrode layer having a stripe electrode composed of a plurality of line electrodes being arranged in given pitches for retrieving the electric charges for a latent image from the electric accumulator. Here, the first signal detecting device may also include a multiplexer for switching the signal components concerning the charge signals outputted from the respective line electrodes depending on the respective line electrodes and thereby outputting the signal components to the converting means.

Here, the foregoing "given pitches" refer to pixel pitches.

A second signal detecting device of the present invention includes an integrating amplifier for accumulating charge signals and for outputting electric signals corresponding to amounts of the accumulated electric charges, switching means for switching the integrating amplifier between an accumulator mode and a reset mode, first signal retaining means for retaining a first electric signal outputted immediately after the integrating amplifier is switched to the accumulator mode, second signal retaining means for retaining a second electric signal outputted from the integrating amplifier immediately before the integrating amplifier is switched to the reset mode by the switching means, a multiplexer for switching and thereby outputting the first electric signal retained by the first signal retaining means and the second electric signal retained by the second signal retaining means respectively, and converting means for converting the first electric signal and the second electric signal outputted from the multiplexer respectively into digital signals and thereby outputting the digital signals.

Here, the second signal detecting device performs the so-called digital correlated double sampling. Accordingly, it is preferred that the second signal detecting device conducts signal detection in accordance with the second signal detecting method.

Moreover, in the second signal detecting device, the integrating amplifier, the first signal retaining means and the second signal retaining means may be respectively provided on each of line electrodes of an image detector. Here, the image detector is formed by serially stacking a first electrode layer having transmissivity with respect to an electromagnetic wave for recording, a recording photoconductive layer which takes on conductivity by receiving irradiation of the electromagnetic wave for recording transmitted through the first electrode layer, an electric accumulator for accumulating electric charges generated in the recording photoconductive layer by irradiation of the electromagnetic wave for recording as electric charges for a latent image, a retrieving photoconductive layer which takes on conductivity by receiving irradiation of an electromagnetic wave for retrieval, and a second electrode layer having a stripe electrode composed of a plurality of line electrodes being arranged in given pitches for retrieving the electric charges for a latent image from the electric accumulator. Here, in the second signal detecting device, the multiplexer may switch the first electric signal and the second electric signal concerning the charge signal outputted from the respective line electrodes depending on the respective line electrodes and thereby may output the first and second electric signals to the converting means.

A third signal detecting device of the present invention includes an integrating amplifier for accumulating charge signals and for outputting electric signals corresponding to amounts of the accumulated electric charges, switching means for switching the integrating amplifier between an accumulator mode and a reset mode, first signal retaining means for retaining a first electric signal outputted immediately after the integrating amplifier is switched to the accumulator mode, second signal retaining means for retaining a second electric signal outputted from the integrating amplifier immediately before the integrating amplifier is switched to the reset mode by the switching means, first converting means for converting the first electric signal retained by the first signal retaining means into a digital signal, and second converting means for converting the second electric signal retained by the second signal retaining means into a digital signal.

Here, the third signal detecting device performs the so-called digital correlated double sampling as similar to the second signal detecting device. Accordingly, it is preferred that the third signal detecting device conducts signal detection in accordance with the third signal detecting method.

Moreover, in the third signal detecting device, the integrating amplifier, the first signal retaining means and the second signal retaining means may be respectively provided on each of line electrodes of an image detector. Here, the image detector is formed by serially stacking a first electrode layer having transmissivity with respect to an electromagnetic wave for recording, a recording photoconductive layer which takes on conductivity by receiving irradiation of the electromagnetic wave for recording transmitted through the first electrode layer, an electric accumulator for accumulating electric charges generated in the recording photoconductive layer by irradiation of the electromagnetic wave for recording as electric charges for a latent image, a retrieving photoconductive layer which takes on conductivity by receiving irradiation of an electromagnetic wave for retrieval, and a second electrode layer having a stripe electrode composed of a plurality of line electrodes being arranged in given pitches for retrieving the electric charges for a latent image from the electric accumulator. Here, the third signal detecting device may also include a first multiplexer for switching the first electric signal concerning the charge signal outputted from the respective line electrodes depending on the respective line electrodes and thereby outputting the first electric signal to the first converting means, and a second multiplexer for switching the second electric signal concerning the charge signal outputted from the respective line electrodes depending on the respective line electrodes and thereby outputting the second electric signal to the second converting means.

According to the first signal detecting method and the first signal detecting device of the present invention, a signal detecting method and a signal detecting device are provided for performing the so-called analog correlated double sampling, in which the signal component being found concerning the first charge signal is retained and the retained signal component is converted into a digital signal. Then, the integrating amplifier is switched to the accumulator mode after completing accumulation concerning the first charge signal but before completing conversion of the signal component into the digital signal so as to initiate accumulation concerning the second charge signal. Accordingly, it is possible to initiate accumulation concerning the second charge signal without waiting for completion of conversion of the signal component into the digital signal. In this way, it is possible to shorten the process time correspondingly. Otherwise, if the shortened time is allotted to accumulation by the integrating amplifier, it is possible to lengthen the time for retrieving the charge signal. Accordingly, it is possible to enhance an S/N ratio of the signal to be detected.

Moreover, in the case of retrieving a radiation image by scanning a solid state radiation image detector with retrieving light, for example, it is also possible to perform accumulation of the charge signal during the conversion without overlooking the charge signal retrieved during the conversion of the signal component into the digital signal as observed in the prior art. Accordingly, it is possible to enhance an S/N ratio of the retrieved radiation image.

According to the second signal detecting method and the second signal detecting device of the present invention, a signal detecting method and a signal detecting device are provided for performing the so-called digital correlated double sampling, in which the first electric signal concerning the first charge signal is retained by the first signal retaining means, and the second electric signal concerning the first charge signal is retained by the second signal retaining means. Moreover, the integrating amplifier is switched to the accumulator mode after completing accumulation concerning the first charge signal but before completing conversion of the retained second electric signal into the second digital signal so as to initiate accumulation concerning the second charge signal. Accordingly, it is possible to initiate accumulation concerning the second charge signal without waiting for completion of conversion of the second electric signal into the digital signal. In this way, it is possible to shorten the process time correspondingly. Otherwise, if the shortened time is allotted to accumulation by the integrating amplifier, it is possible to lengthen time for retrieving the charge signal. Accordingly, it is possible to enhance an S/N ratio of the signal to be detected.

Moreover, in the case of retrieving a radiation image by scanning a solid state radiation image detector with retrieving light, for example, it is also possible to perform accumulation of the charge signal during the conversion without overlooking the charge signal retrieved during the conversion of the second electric signal into the digital signal as observed in the prior art. Accordingly, it is possible to enhance an S/N ratio of the retrieved radiation image.

According to the third signal detecting method and the third signal detecting device, a signal detecting method and a signal detecting device are provided for performing the so-called digital correlated double sampling, in which the first electric signal is retained by the first signal retaining means, and the retained first electric signal is converted into the first digital signal by the first converting means. Then, the second electric signal is retained by the second signal retaining means, and the retained second electric signal is converted into the second digital signal by the second converting means. Moreover, the integrating amplifier is switched to the accumulator mode after completing accumulation concerning the first charge signal but before completing conversion of the retained second electric signal into the second digital signal so as to initiate accumulation concerning the second charge signal, and the first electric signal concerning the second charge signal outputted from the integrating amplifier immediately after the integrating amplifier is switched to the accumulator mode. Thereafter, the first electric signal concerning the second charge signal is converted into the first digital signal and outputted before completion of conversion of the second electric signal concerning the first charge signal into the second digital signal. Accordingly, as similar to the second signal detecting method and the second signal detecting device, it is possible to initiate accumulation concerning the second charge signal without waiting for completion of conversion of the second electric signal into the digital signal. In this way, it is possible to shorten the process time correspondingly.

In addition, conversion of the second electric signal concerning the first charge signal into the digital signal and conversion of the first electric signal concerning the second charge signal into the digital signal are respectively performed in parallel by the different converting means. Accordingly, it is possible to lengthen time for conversion processing correspondingly. In this way, it is possible to use relatively low-speed and low-cost devices as the converting means.

BRIEF DESCRIPTION OF THE DRAWINGS

FIGS. 1A, 1B and 1C are schematic constitutional views collectively showing a radiation image retrieving apparatus adopting a signal detecting device according to a first embodiment of the present invention.

DESCRIPTION OF THE PREFERRED EMBODIMENTS

Figure 2:
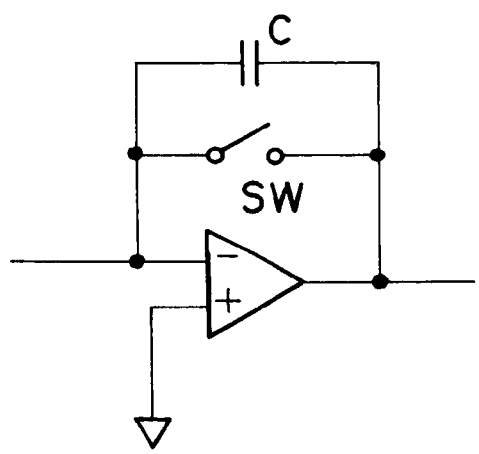
FIG. 2 is a diagram showing an integrating amplifier for use in the signal detecting device of the present invention.

Now, specific embodiments of the present invention will be described with reference to the accompanying drawings.

FIGS. 1A, 1B and 1C are schematic constitutional views collectively showing a radiation image retrieving apparatus adopting a signal detecting device according to a first embodiment of the present invention. The radiation image retrieving apparatus is designed to use a solid state radiation image detector 10 (hereinafter referred to as the "detector") and to retrieve radiation image information out of the solid state radiation image detector 10. Note that FIG. 1A is a perspective view showing the detector 10; FIG. 1B is an X-Z cross-sectional view of the position indicated with an arrow P in FIG. 1A; and FIG. 1C is an X-Y cross-sectional view of the position indicated with an arrow Q in FIG. 1A.

The detector 10 is formed by serially stacking a first electrode layer 11 having transmissivity with respect to a recording radiation, a recording photoconductive layer 12 which takes on conductivity by receiving irradiation of the recording radiation transmitted through the first electrode layer 11, a charge transport layer 13 acting substantially as an insulator with respect to electric charges of the same polarity as electric charges to be charged on the first electrode layer and acting substantially as a conductor with respect to electric charges of the reverse polarity to the foregoing polarity, a retrieving photoconductive layer 14 which takes on conductivity by receiving irradiation of an electromagnetic wave for retrieval, and a second electrode layer 15 having transmissivity with respect to the electromagnetic wave for retrieval. An electric accumulator is formed on an interface between the recording photoconductive layer 12 and the charge transport layer 13.

An electrode of the second electrode layer 15 constitutes a stripe electrode 16, in which multiple elements (line electrodes) 16a (FIG. 1A illustrates five lines from C1 to C5) are arranged in a stripe.

Moreover, in the radiation image retrieving apparatus, a line light source 90 using an LED array or the like is disposed on the second electrode layer 15 side of the detector 10 as shown in FIG. 1A. The line light source 90 is designed to irradiate an entire surface of the second electrode layer 15 two-dimensionally by emitting linear retrieving light extending in an orthogonal direction (a main-scanning direction) to a longitudinal direction (a sub-scanning direction) of the elements 16a and by moving in the sub-scanning direction.

A readout circuit 30 includes an integrating amplifier unit 35 having integrating amplifiers 35a to 35e respectively connected to the respective elements 16a for accumulating charge signals to be outputted from the respective elements 16a and outputting electric signals corresponding to amounts of the accumulated charge signals, switching means 40 for switching each of the integrating amplifiers between an accumulator mode and a reset mode, a first signal retention unit 31 having first signal retaining means 31a to 31e for retaining the electric signals outputted from the integrating amplifiers, a differentiator circuit unit 32 having differentiator circuits 32a to 32e for finding differences between the electric signals outputted from the integrating amplifiers and the electric signals retained in the first signal retention unit 31 and thereby outputting the differences as signal components, a second signal retention unit 33 having second signal retaining means 33a to 33e for retaining the signal components outputted from the differentiator circuits, and a multiplexer 34 for switching and thereby outputting the signal components being outputted from the respective second signal retaining means of the second signal retention unit 33 depending on the respective second signal retaining means.

Moreover, controlling means 60 is designed to control the readout circuit 30 and an A/D converter 50. The controlling method thereof will be described later.

Next, description will be made regarding an operation of retrieving the radiation image information recorded on the detector 10 by use of the radiation image retrieving apparatus adopting the signal detecting device according to the first embodiment of the present invention.

In the detector 10, electric charges generated in the recording photoconductive layer 12 owing to irradiation of the recording light carrying the radiation image information are accumulated in the electric accumulator formed on the interface between the recording photoconductive layer 12 and the charge transport layer 13 as electric charges for a latent image.

When the linear retrieving light is irradiated from the line light source 90, charge pairs are generated inside the retrieving photoconductive layer 14. Then electric currents are generated owing to the charge pairs moving toward the electric accumulator and the stripe electrode 16 of the second electrode layer 15. Such an electric current is detected by the integrating amplifiers of the integrating amplifier unit 35. In this event, the first electrode layer 11 and the stripe electrode 16 of the second electrode layer 15 are connected to each other via an imaginary short of the integrating amplifiers.

To be more precise, the integrating amplifier has a constitution as shown in FIG. 2. The integrating amplifier is designed to detect signals by means of accumulating an electric charge flowing out of the line electrode into a capacitor C. Moreover, the above-mentioned accumulation of the electric charge is performed when a switch SW is turned off (an accumulator mode). Meanwhile, the accumulated electric charge is discharged when the switch SW is turned on and an electric signal corresponding to the accumulated electric charge is outputted and then the integrating amplifier is reset (a reset mode). Such switching operations of the switch SW are controlled by the switching means 40.

Figure 8:
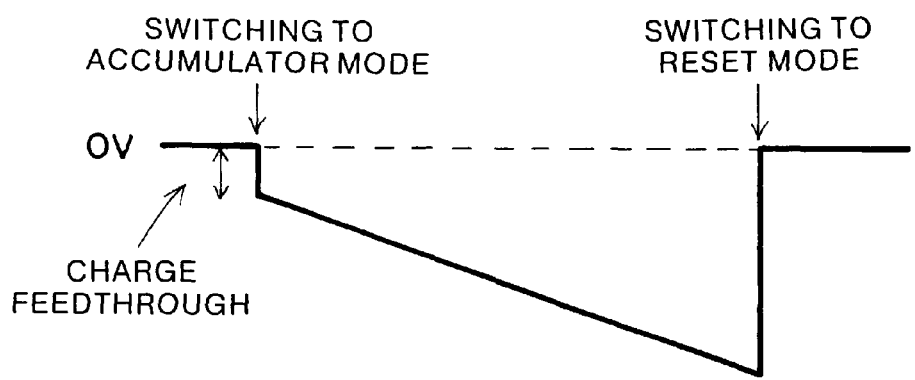
FIG. 8 is a graph for describing a charge feedthrough.
Figure 9:
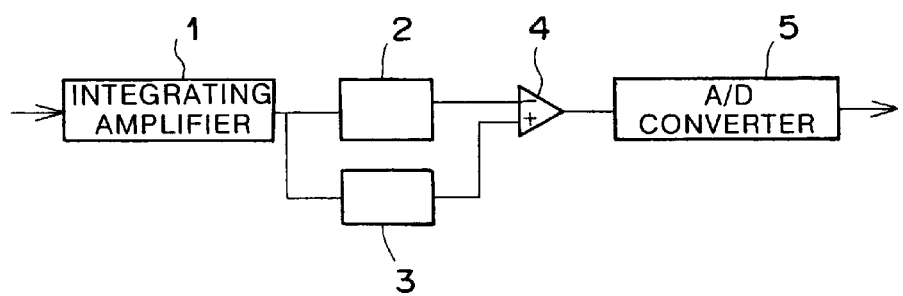
FIG. 9 is a view showing a conventional readout circuit for performing analog correlated double sampling.
Figure 10:
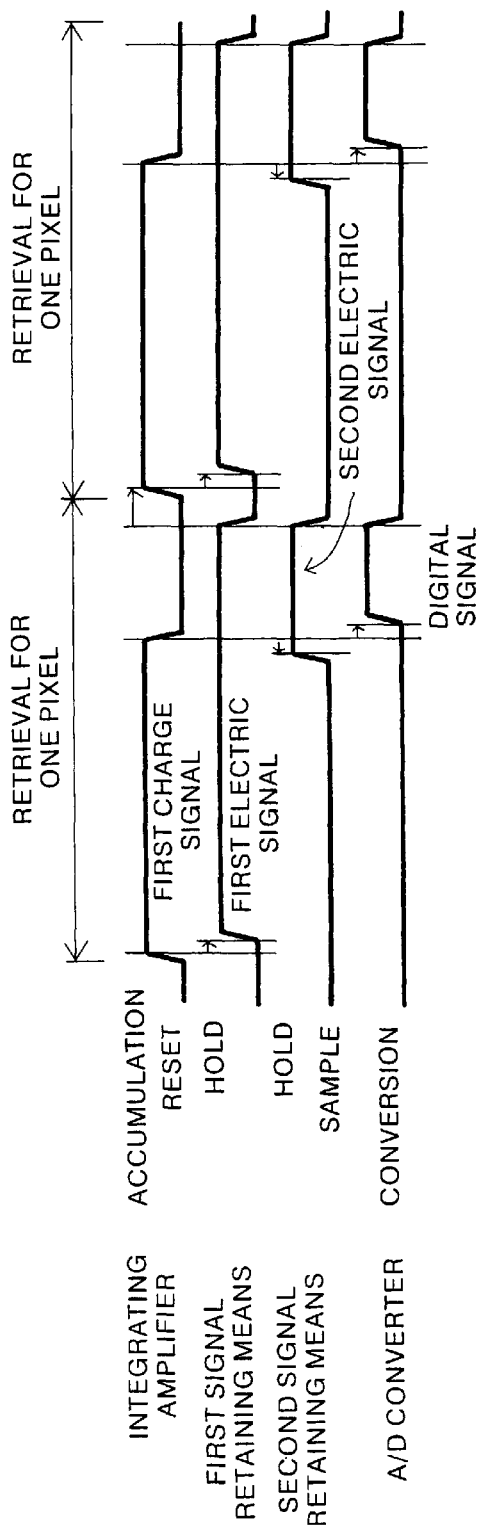
FIG. 10 is a timing chart showing control timing for an integrating amplifier, first signal retaining means, second signal retaining means and an A/D converter in the readout circuit shown in FIG. 9.
Figure 11:
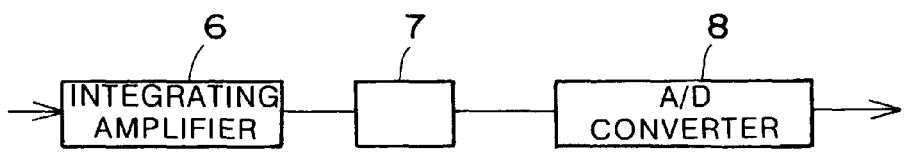
FIG. 11 is a view showing a conventional readout circuit for performing digital correlated double sampling.
Figure 12:
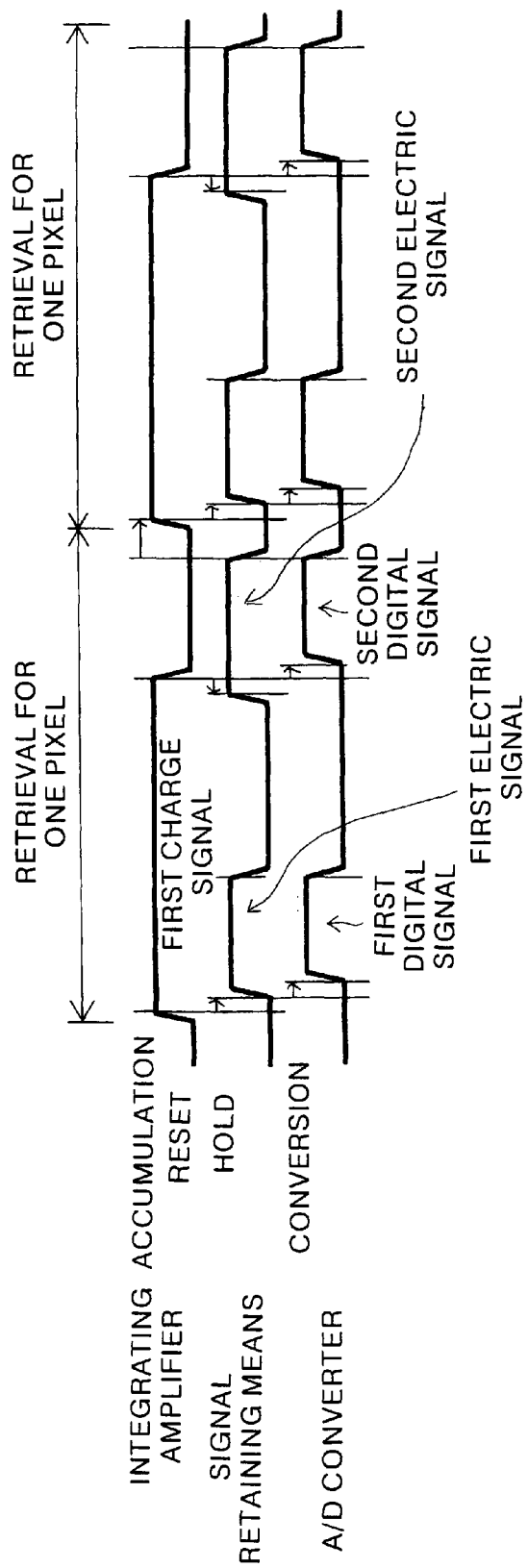
FIG. 12 is a timing chart showing control timing for an integrating amplifier, signal retaining means and an A/D converter in the readout circuit shown in FIG. 11.

Here, in the event immediately after the integrating amplifier is switched from the reset mode to the accumulator mode by the switching means 40, an offset called a charge feedthrough attributable to capacitance of the switch or the like is outputted as shown in FIG. 8. The charge feedthrough is not always constant but is fluctuant; therefore, it is not possible to obtain accurate signal components corresponding to the radiation image information if processing is applied that subtracts an uniform offset. Therefore, correlated double sampling is applied in order to eliminate an influence of the charge feedthrough. The correlated double sampling refers to processing, which can eliminate the influence of the charge feedthrough by means of measuring a difference between the electric signal to be outputted immediately after the integrating amplifier is switched to the accumulator mode and the electric signal to be outputted immediately before the integrating amplifier is switched to the reset mode, and by defining the difference as a signal component.

The radiation image retrieving apparatus of the present invention is designed to perform the correlated double sampling and to effectuate shortening of a processing time period from initiating accumulation of the charge signal by the integrating amplifier to outputting the digital signal corresponding to the signal component from the A/D converter 50.

In the following, description will be made in detail regarding the processes performed between initiating accumulation of the charge signal by the integrating amplifier and outputting the digital signal corresponding to the signal component by the A/D converter 50.

Figure 3:
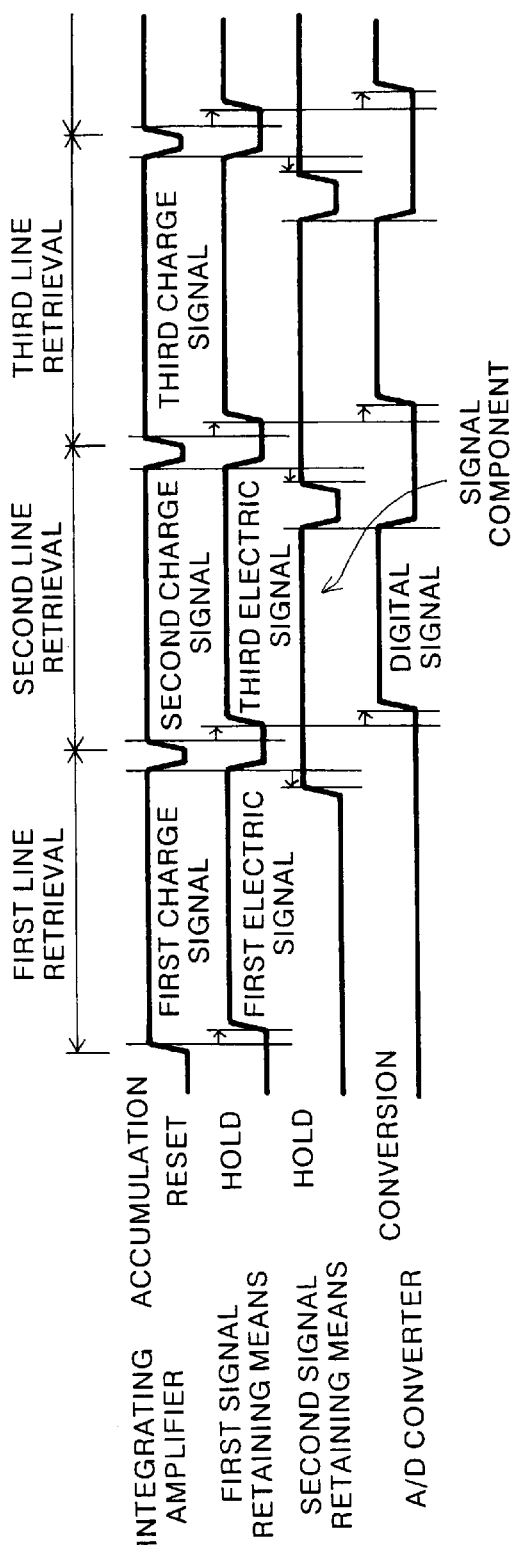
FIG. 3 is a timing chart showing control timing for an integrating amplifier unit, a first signal retention unit, a second signal retention unit and an A/D converter in the radiation image retrieving apparatus shown in FIGS. 1A, 1B and 1C.

FIG. 3 is a timing chart showing control timing for the integrating amplifier unit 35, the first signal retention unit 31, the second signal retention unit 33 and the A/D converter 50 in the radiation image retrieving apparatus.

As shown in FIG. 3, the integrating amplifier of the integrating amplifier unit 35 is first switched to the accumulator mode by the switching means 40, thus initiating accumulation of a first charge signal flowing out of the element 16a owing to irradiation of the retrieving light on a first line. Then, a first electric signal outputted from the integrating amplifier immediately after switching to the accumulator mode is retained by the first signal retaining means of the first signal retention unit 31. Next, after passage of a sufficient time period for accumulation of the first charge signal in the integrating amplifier, a difference between a second electric signal outputted from the integrating amplifier immediately before switching to the reset mode and the first electric signal retained by the first signal retaining means is found by the differentiator circuit of the differentiator circuit unit 32, and a result thereof is retained by the second signal retaining means of the second signal retention unit 33 as a signal component. Thereafter, the integrating amplifier unit 35 is switched to the reset mode and then switched again to the accumulator mode, thus initiating accumulation of a second charge signal flowing out of the line electrode owing to irradiation of the retrieving light on a second line subsequent to the first line. Thereafter, a third electric signal outputted from the integrating amplifier immediately after switching to the accumulator mode again is retained by the first signal retaining means, and then the signal component retained by the second signal retaining means is outputted to the A/D converter 50. The A/D converter 50 further converts the signal component into a digital signal, and the digital signal is outputted thereafter. In this event, the multiplexer 34 switches among the respective second signal retaining means 33a to 33e in sequence, whereby the multiplexer 34 outputs the signal components retained by the respective second signal retaining means to the A/D converter 50 in sequence. Then, after passage of a sufficient time period for accumulation of the second charge signal in the integrating amplifier, a difference between a fourth electric signal outputted from the integrating amplifier immediately before switching to the reset mode and the third electric signal retained by the first signal retaining means is found by the differentiator circuit of the differentiator circuit unit 32, and a result thereof is retained by the second signal retaining means of the second signal retention unit 33 as a signal component of the second charge signal. Next, accumulation of a third charge signal flowing out of the line electrode owing to irradiation of the retrieving light on a third line is initiated. However, subsequent processes are carried out by repeating the above-described processes starting from initiation of accumulation of the first charge signal. By retrieving the last line accordingly, the radiation image information accumulated in the detector 10 can be retrieved as digital signals processed by correlated double sampling.

According to the above-described radiation image retrieving apparatus, the signal component being found concerning the first charge signal is retained and the retained signal component is converted into the digital signal. Moreover, the integrating amplifier is switched to the accumulator mode after completing accumulation concerning the first charge signal but before completing conversion of the signal component into the digital signal so as to initiate accumulation concerning the second charge signal. Accordingly, it is possible to initiate accumulation concerning the second charge signal without waiting for completion of conversion of the signal component into the digital signal. In this way, it is possible to shorten the process time correspondingly. Otherwise, if the shortened time is allotted to accumulation by the integrating amplifier, it is possible to lengthen time for retrieving the charge signal. Accordingly, it is possible to enhance an S/N ratio of the signal to be detected.

Moreover, it is also possible to perform accumulation of the charge signal during the conversion without overlooking the charge signal retrieved during the conversion of the signal component into the digital signal as observed in the prior art. Accordingly, it is possible to enhance an S/N ratio of the retrieved radiation image.

Next, description will be made regarding a radiation image retrieving apparatus adopting a signal detecting device according to a second embodiment of the present invention. This radiation image retrieving apparatus is also designed to use the detector 10 as similar to the radiation image retrieving apparatus according to the first embodiment, and to retrieve radiation image information out of the detector 10.

As similar to the radiation image retrieving apparatus according to the first embodiment, this radiation image retrieving apparatus is also designed to perform correlated double sampling and to effectuate shortening of a processing time period from initiating accumulation of a charge signal by an integrating amplifier to outputting a digital signal from an A/D converter. However, this radiation image retrieving apparatus performs the so-called digital correlated double sampling (DCDS), in which an electric signal outputted immediately after the integrating amplifier is switched to an accumulator mode and an electric signal outputted immediately before the integrating amplifier is switched to a reset mode are respectively converted into digital signals with the A/D converter, and then a difference therebetween is computed by software in an image processing device or the like, which is disposed subsequently to the A/D converter. On the contrary, the processing to be carried out by the radiation image retrieving apparatus according to the first embodiment is referred to as the so-called analog correlated double sampling (ACDS).

Figure 4:
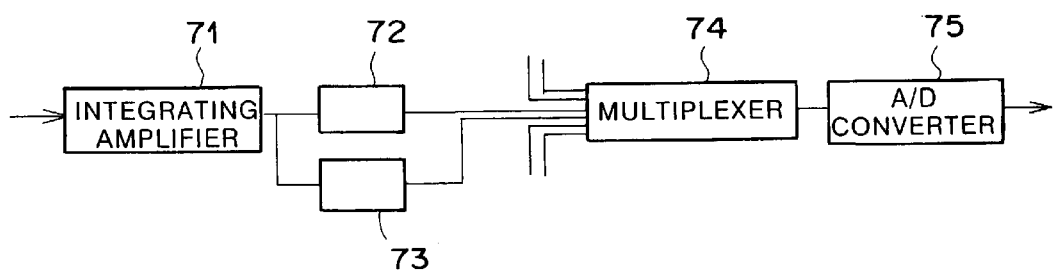
FIG. 4 is a schematic constitutional view showing a radiation image retrieving apparatus adopting a signal detecting device according to a second embodiment of the present invention.

FIG. 4 is a schematic constitutional view of part of a readout circuit of this radiation image retrieving apparatus, which is different from the corresponding readout circuit in the radiation image retrieving apparatus according to the first embodiment. Since other part of the constitution is similar to those of the radiation image retrieving apparatus according to the first embodiment, description thereof will be omitted herein. In addition, whereas the integrating amplifier, first signal retaining means and second signal retaining means are provided respectively on each of elements 16a of the detector 10, FIG. 4 illustrates only the integrating amplifier, the first signal retaining means and the second signal retaining means concerning one element 16a required for explanation of this embodiment.

As shown in FIG. 4, a readout circuit 70 of this radiation image retrieving device includes an integrating amplifier 71 connected to each element 16a, first signal retaining means 72 for retaining a first electric signal outputted from the integrating amplifier immediately after the integrating amplifier is switched to an accumulator mode, second signal retaining means 73 for retaining a second electric signal outputted from the integrating amplifier immediately before the integrating amplifier is switched to a reset mode, and a multiplexer 74 for switching and thereby outputting the first electric signal retained by the first signal retaining means 72 and the second electric signal retained by the second signal retaining means 73 respectively.

An A/D converter 75 converts the first electric signal and the second electric signal outputted from the multiplexer 74 respectively into a first digital signal and a second digital signal, and outputs the digital signals accordingly.

Next, description will be made regarding an operation of retrieving radiation image information recorded on the detector 10 by use of the radiation image retrieving apparatus adopting the signal detecting device according to the second embodiment of the present invention. Here, description will be made in detail regarding processes from initiating accumulation of electric charges with the integrating amplifier to outputting the digital signal from the A/D converter 75, which refer to a different operation from the operation of the radiation image retrieving apparatus according to the first embodiment.

Figure 5:
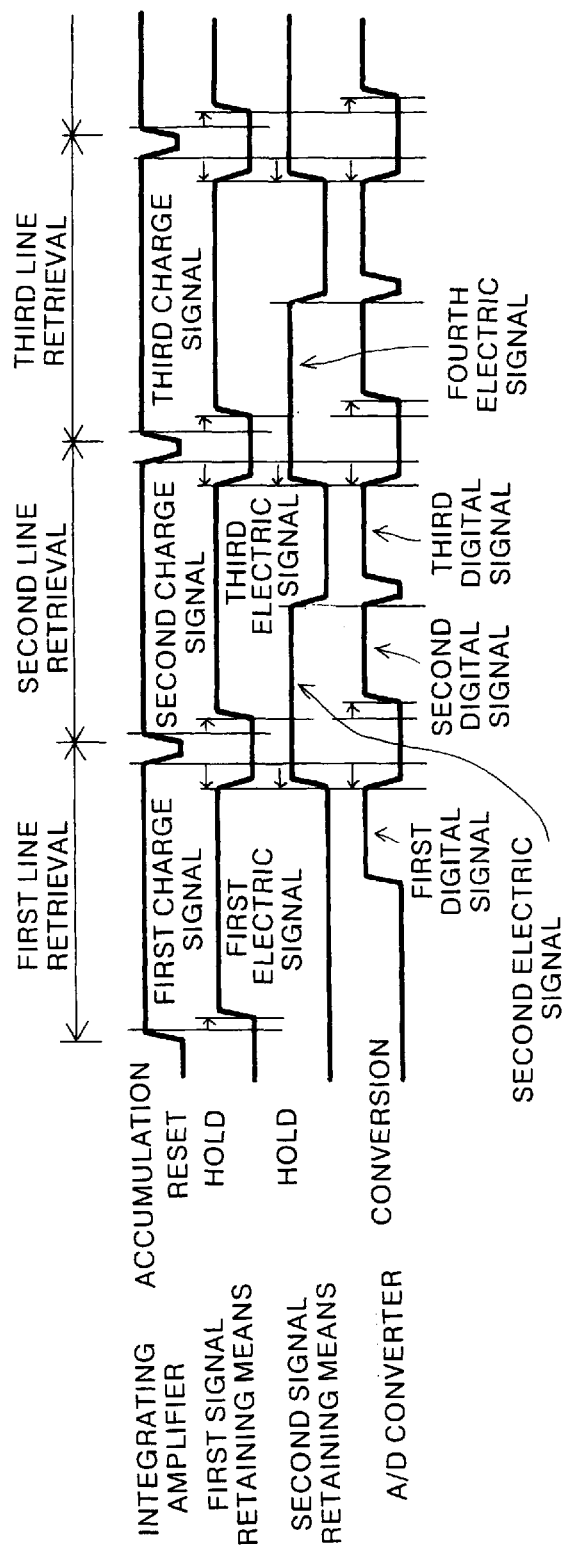
FIG. 5 is a timing chart showing control timing for an integrating amplifier unit, a first signal retention unit, a second signal retention unit and an A/D converter in the radiation image retrieving apparatus shown in FIG. 4.

FIG. 5 is a timing chart showing control timing for the integrating amplifier 71, the first signal retaining means 72, the second signal retaining means 73 and the A/D converter 75 in this radiation image retrieving apparatus.

As shown in FIG. 5, the integrating amplifier 71 is firstly switched to the accumulator mode by switching means 40, thus initiating accumulation of a first charge signal flowing out of the element 16a owing to irradiation of retrieving light on a first line. Then, the first electric signal outputted from the integrating amplifier immediately after switching to the accumulator mode is retained by the first signal retaining means 72. Next, the first electric signal retained by the first signal retaining means 72 is converted into the first digital signal with the A/D converter 75. In this event, the multiplexer 74 switches among the respective first signal retaining means provided corresponding to the respective elements 16a in sequence, whereby the multiplexer 74 outputs the first electric signals retained by the respective first signal retaining means to the A/D converter 75. Then, after passage of a sufficient time period for accumulation of the first charge signal in the integrating amplifier, the second electric signal outputted from the integrating amplifier immediately before switching to the reset mode is retained by the second signal retaining means 73. Thereafter, the integrating amplifier 71 is switched to the reset mode and then switched again to the accumulator mode, thus initiating accumulation of a second charge signal flowing out of the line electrode owing to irradiation of the retrieving light on a second line subsequent to the first line. Thereafter, a third electric signal outputted from the integrating amplifier immediately after switching to the accumulator mode again is retained by the first signal retaining means, and then the second electric signal retained by the second signal retaining means is outputted to the A/D converter 75. The A/D converter 75 further converts the second electric signal into the second digital signal. Thereafter, a third electric signal retained by the first signal retaining means is outputted and converted into a third digital signal with the A/D converter 75, and then the third electric signal is outputted. In this event, the multiplexer 74 switches among the respective second signal retaining means provided corresponding to the respective elements 16a in sequence, whereby the multiplexer 74 outputs the retained second electric signals to the A/D converter 75. Furthermore, the multiplexer 74 switches among the respective first signal retaining means provided corresponding to the respective elements 16a in sequence, whereby the multiplexer 74 outputs the third electric signals retained by the respective first signal retaining means to the A/D converter 75. Then, after passage of a sufficient time period for accumulation of the second charge signal in the integrating amplifier, a fourth electric signal outputted from the integrating amplifier immediately before switching to the reset mode is retained by the second signal retaining means. Next, accumulation of a third charge signal flowing out of the line electrode owing to irradiation of the retrieving light on a third line is initiated. However, subsequent processes are carried out by repeating the above-described processes starting from initiation of accumulation of the first charge signal. By retrieving the last line accordingly, the radiation image information accumulated in the detector 10 can be retrieved as digital signals processed by correlated double sampling.

According to the above-described radiation image retrieving apparatus, the first electric signal concerning the first charge signal is retained by the first signal retaining means and the second electric signal concerning the first charge signal is retained by the second signal retaining means. Moreover, the integrating amplifier is switched to the accumulator mode after completing accumulation concerning the first charge signal but before completing conversion of the retained second electric signal into the second digital signal so as to initiate accumulation concerning the second charge signal. Accordingly, it is possible to initiate accumulation concerning the second charge signal without waiting for completion of conversion of the second electric signal into the digital signal. In this way, it is possible to shorten the process time correspondingly. Otherwise, if the shortened time is allotted to accumulation by the integrating amplifier, it is possible to lengthen time for retrieving the charge signal. Accordingly, it is possible to enhance an S/N ratio of the signal to be detected.

Moreover, it is also possible to perform accumulation of the charge signal during the conversion without overlooking the charge signal retrieved during the conversion of the second electric signal into the digital signal as observed in the prior art. Accordingly, it is possible to enhance an S/N ratio of the retrieved radiation image.

Next, description will be made regarding a radiation image retrieving apparatus adopting a signal detecting device according to a third embodiment of the present invention. This radiation image retrieving apparatus is also designed to use the detector 10 as similar to the radiation image retrieving apparatus according to the first embodiment, and to retrieve radiation image information out of the detector 10.

As similar to the radiation image retrieving apparatus according to the second embodiment, this radiation image retrieving apparatus is also designed to perform the so-called digital correlated double sampling (DCDS).

Figure 6:
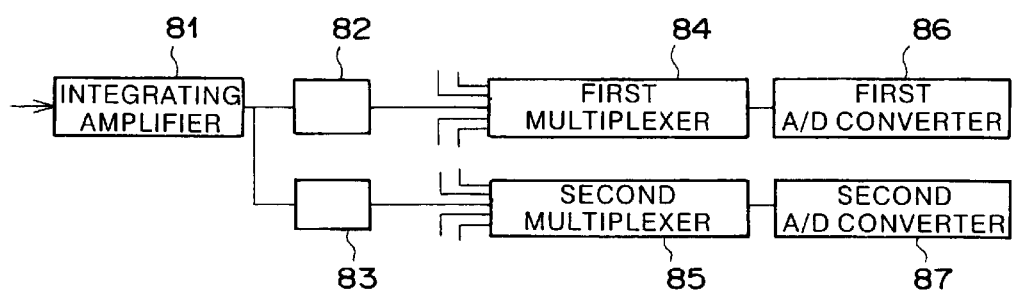
FIG. 6 is a schematic constitutional view showing a radiation image retrieving apparatus adopting a signal detecting device according to a third embodiment of the present invention.

FIG. 6 is a schematic constitutional view of part of a readout circuit of this radiation image retrieving apparatus, which is different from the corresponding readout circuit in the radiation image retrieving apparatus according to the first embodiment. Since other part of the constitution is similar to those of the radiation image retrieving apparatus according to the first embodiment, description thereof will be omitted herein. In addition, whereas an integrating amplifier 81, first signal retaining means 82 and second signal retaining means 83 are provided respectively on each of elements 16a of the detector 10, FIG. 6 illustrates only the integrating amplifier 81, the first signal retaining means 82 and the second signal retaining means 83 concerning one element 16a required for explanation of this embodiment.

As shown in FIG. 6, a readout circuit 80 of this radiation image retrieving apparatus includes the integrating amplifier 81 connected to each element 16a, the first signal retaining means 82 for retaining a first electric signal outputted from the integrating amplifier 81 immediately after the integrating amplifier 81 is switched to an accumulator mode, the second signal retaining means 83 for retaining a second electric signal outputted from the integrating amplifier immediately before the integrating amplifier is switched to a reset mode, a first A/D converter 86 for converting the first electric signal retained by the first signal retaining means 82 into a digital signal, a second A/D converter 87 for converting the second electric signal retained by the second signal retaining means 83 into a digital signal, a first multiplexer 84 for switching the first electric signal retained by the first signal retaining means 82 depending on each of the elements 16a and for outputting the first electric signal to the first A/D converter 86, and a second multiplexer 85 for switching the second electric signal retained by the second signal retaining means 83 depending on each of the elements 16a and for outputting the second electric signal to the second A/D converter 87.

Next, description will be made regarding an operation of retrieving radiation image information recorded on the detector 10 by use of the radiation image retrieving apparatus adopting the signal detecting device according to the third embodiment of the present invention. Here, description will be made in detail regarding processes from initiating accumulation of electric charges with the integrating amplifier to outputting the digital signal from the first and second A/D converters 86 and 87, which refer to a different operation from the operation of the radiation image retrieving apparatus according to the first embodiment.

Figure 7:
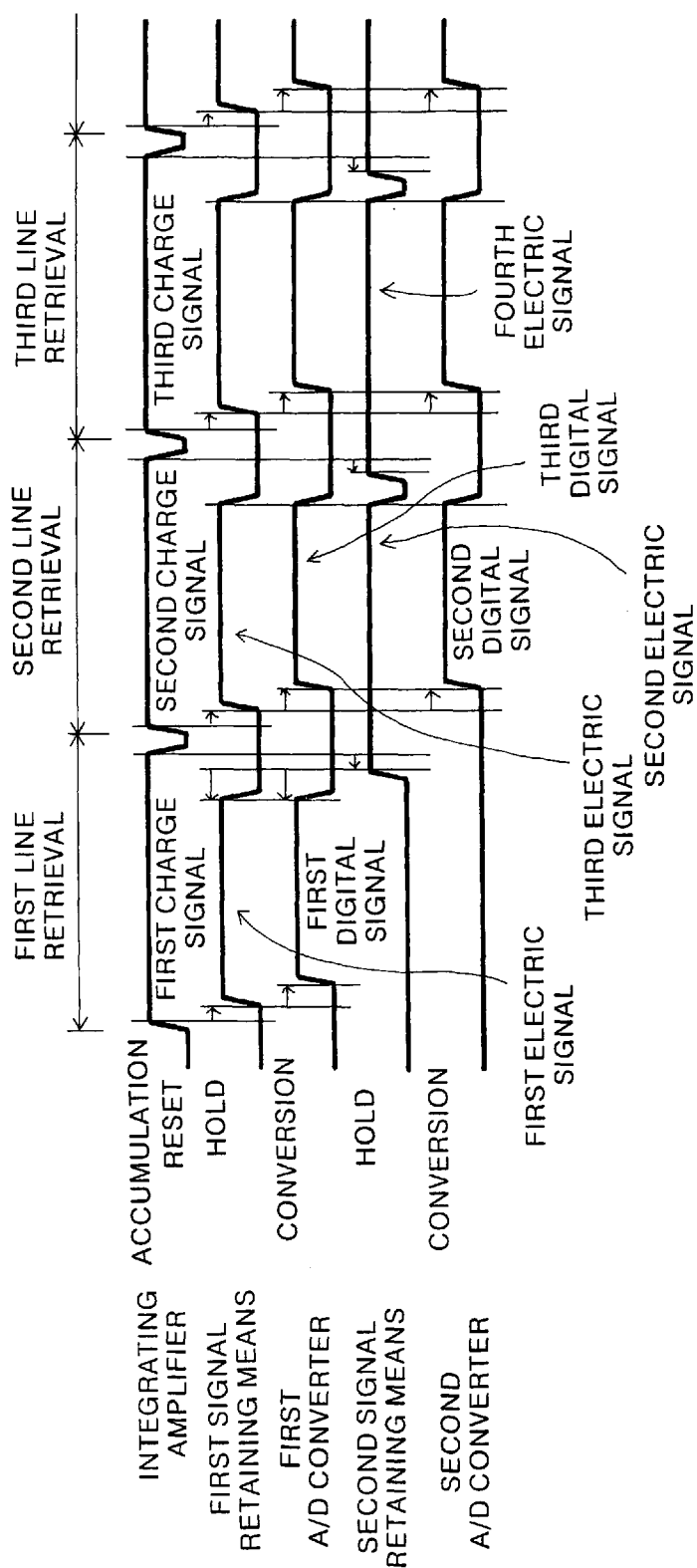
FIG. 7 is a timing chart showing control timing for an integrating amplifier unit, a first signal retention unit, a second signal retention unit and A/D converters in the radiation image retrieving apparatus shown in FIG. 6.

FIG. 7 is a timing chart showing control timing for the integrating amplifier 81, the first signal retaining means 82, the second signal retaining means 83 and the first and second A/D converters 86 and 87 in this radiation image retrieving apparatus.

As shown in FIG. 7, the integrating amplifier 81 is firstly switched to the accumulator mode by switching means 40, thus initiating accumulation of a first charge signal flowing out of the element 16a owing to irradiation of retrieving light on a first line. Then, the first electric signal outputted from the integrating amplifier immediately after switching to the accumulator mode is retained by the first signal retaining means 82. Next, the first electric signal retained by the first signal retaining means 82 is converted into a first digital signal with the first A/D converter 86. In this event, the first multiplexer 84 switches among the respective first signal retaining means provided corresponding to the respective elements 16a in sequence, whereby the first multiplexer 84 outputs the first electric signals retained by the respective first signal retaining means to the first A/D converter 86. Then, after passage of a sufficient time period for accumulation of the first charge signal in the integrating amplifier, the second electric signal outputted from the integrating amplifier immediately before switching to the reset mode is retained by the second signal retaining means 83. Thereafter, the integrating amplifier 81 is switched to the reset mode and then switched again to the accumulator mode, thus initiating accumulation of a second charge signal flowing out of the line electrode owing to irradiation of the retrieving light on a second line subsequent to the first line. Thereafter, a third electric signal outputted from the integrating amplifier immediately after switching to the accumulator mode again is retained by the first signal retaining means 82, and then the second electric signal retained by the second signal retaining means 87 is outputted to the second A/D converter 87. The A/D converter 87 further converts the second electric signal into a second digital signal. Thereafter, a third electric signal retained by the first signal retaining means 82 is outputted and converted into a third digital signal with the first A/D converter 86, and then the third digital signal is outputted. In this event, the first multiplexer 84 switches among the respective first signal retaining means 82 provided corresponding to the respective elements 16a in sequence, whereby the first multiplexer 84 outputs the third electric signals retained by the respective first signal retaining means 82 to the first A/D converter 86. Meanwhile, the second multiplexer 85 switches among the respective second signal retaining means 83 provided corresponding to the respective elements 16a in sequence, whereby the second multiplexer 85 outputs the second electric signals retained by the respective second signal retaining means 83 to the second A/D converter 87. Then, after passage of a sufficient time period for accumulation of the second charge signal in the integrating amplifier, a fourth electric signal outputted from the integrating amplifier immediately before switching to the reset mode is retained by the second signal retaining means 83. Next, accumulation of a third charge signal flowing out of the line electrode owing to irradiation of the retrieving light on a third line is initiated. However, subsequent processes are carried out by repeating the above-described processes starting from initiation of accumulation of the first charge signal. By retrieving the last line accordingly, the radiation image information accumulated in the detector 10 can be retrieved as digital signals processed by correlated double sampling.

According to the above-described radiation image retrieving apparatus, the first electric signal is retained by the first signal retaining means and the retained first electric signal is converted into the first digital signal with the first converting means. Meanwhile, the second electric signal is retained by the second signal retaining means and the retained second electric signal is converted into the second digital signal with the second converting means. Moreover, the integrating amplifier is switched to the accumulator mode after completing accumulation concerning the first charge signal but before completing conversion of the retained second electric signal into the second digital signal with the second converting means so as to initiate accumulation concerning the second charge signal. Furthermore, the first electric signal concerning the second charge signal outputted from the integrating amplifier immediately after the integrating amplifier is switched to the accumulator mode is retained and then the first electric signal concerning the second charge signal is converted into the first digital signal and outputted prior to completion of conversion of the second electric signal concerning the first charge signal into the second digital signal. Accordingly, as similar to the second signal detecting method and the second signal detecting device, it is possible to initiate accumulation concerning the second charge signal without waiting for completion of conversion of the second electric signal into the digital signal. In this way, it is possible to shorten the process time correspondingly.

In addition, conversion of the second electric signal concerning the first charge signal into the digital signal and conversion of the first electric signal concerning the second charge signal into the digital signal are respectively performed in parallel by the different converting means. Accordingly, it is possible to lengthen time for conversion processing correspondingly. In this way, it is possible to use relatively low-speed and low-price devices as the converting means.

What is claimed is:

1. A signal detecting method of repeating the processes of initiating accumulation of charge signals by switching an integrating amplifier to an accumulator mode, retaining a first electric signal outputted from the integrating amplifier immediately after the integrating amplifier is switched to the accumulator mode, finding a difference between a second electric signal outputted from the integrating amplifier immediately before the integrating amplifier is switched to a reset mode after completing accumulation of the charge signals and the retained first electric signal so as to define the difference as a signal component, and converting the signal component into a digital signal and thereby outputting the digital signal, the signal detecting method comprising the steps of:
   retaining the signal component obtained in connection with a first charge signal;
   converting the retained signal component into the digital signal; and
   switching the integrating amplifier to the accumulator mode after completing accumulation concerning the first charge signal but before completing conversion into the digital signal so as to initiate accumulation concerning a second charge signal.

2. A signal detecting method of repeating the processes of initiating accumulation of charge signals by switching an integrating amplifier to an accumulator mode, retaining a first electric signal outputted from the integrating amplifier immediately after the integrating amplifier is switched to the accumulator mode by signal retaining means, converting the retained first electric signal into a first digital signal, retaining a second electric signal outputted from the integrating amplifier immediately before the integrating amplifier is switched to a reset mode after completing accumulation of the charge signals, and converting the retained second signal into a second digital signal and thereby outputting the second digital signal, the signal detecting method comprising the steps of:
   retaining the first electric signal obtained in connection with a first charge signal by first signal retaining means;
   retaining the second electric signal obtained in connection with the first charge signal by second signal retaining means; and
   switching the integrating amplifier to the accumulator mode after completing accumulation concerning the first charge signal but before completing conversion of the retained second electric signal into the second digital signal so as to initiate accumulation concerning a second charge signal.

3. A signal detecting method of repeating the processes of initiating accumulation of charge signals by switching an integrating amplifier to an accumulator mode, retaining a first electric signal outputted from the integrating amplifier immediately after the integrating amplifier is switched to the accumulator mode by signal retaining means, converting the retained first electric signal into a first digital signal by converting means, retaining a second electric signal outputted from the integrating amplifier immediately before the integrating amplifier is switched to a reset mode after completing accumulation of the charge signals, and converting the retained second signal into a second digital signal by the converting means and thereby outputting the second digital signal, the signal detecting method comprising the steps of:
   retaining the first electric signal by first signal retaining means;
   converting the retained first electric signal into a first digital signal by first converting means;
   retaining the second electric signal by second signal retaining means;

converting the retained second electric signal into a second digital signal by second converting means;

switching the integrating amplifier to the accumulator mode after completing the accumulation concerning the first charge signal but before completing conversion of the retained second electric signal into the second digital signal so as to initiate accumulation concerning a second charge signal;

retaining the first electric signal concerning the second charge signal to be outputted from the integrating amplifier immediately after the integrating amplifier is switched to the accumulator mode; and initiating conversion of the first electric signal concerning the second charge signal into the first digital signal before completing conversion of the second electric signal concerning the first charge signal into the second digital signal.

4. A signal detecting device comprising:

an integrating amplifier for accumulating charge signals and for outputting electric signals corresponding to amounts of the accumulated electric charges;

switching means for switching the integrating amplifier between an accumulator mode and a reset mode;

first signal retaining means for retaining a first electric signal outputted immediately after the integrating amplifier is switched to the accumulator mode by the switching means;

a differentiator circuit for finding a difference between a second electric signal outputted from the integrating amplifier immediately before the integrating amplifier is switched to the reset mode by the switching means and the first electric signal retained by the first signal retaining means and thereby outputting the difference as a signal component;

second signal retaining means for retaining the signal component outputted from the differentiator circuit; and converting means for converting the signal component retained by the second signal retaining means into a digital signal.

5. The signal detecting device according to claim 4, wherein the charge signal is retrieved by irradiating an electromagnetic wave for retrieval from a second electrode layer side of an image detector, the image detector being formed by serially stacking a first electrode layer having transmissivity with respect to an electromagnetic wave for recording, a recording photoconductive layer which takes on conductivity by receiving irradiation of the electromagnetic wave for recording transmitted through the first electrode layer, an electric accumulator for accumulating electric charges generated in the recording photoconductive layer by irradiation of the electromagnetic wave for recording as electric charges for a latent image, a retrieving photoconductive layer which takes on conductivity by receiving irradiation of the electromagnetic wave for retrieval, and the second electrode layer having a stripe electrode composed of a plurality of line electrodes being arranged in given pitches for retrieving the electric charges for a latent image from the electric accumulator, the integrating amplifier, the first signal retaining means, the differentiator circuit and the second signal retaining means are respectively provided on each of the line electrodes, and the signal detecting device includes a multiplexer for switching the signal components concerning the charge signals outputted from the respective line electrodes depending on the respective line electrodes and thereby outputting the signal components to the converting means.

6. A signal detecting device comprising:

an integrating amplifier for accumulating charge signals and for outputting electric signals corresponding to amounts of the accumulated electric charges;

switching means for switching the integrating amplifier between an accumulator mode and a reset mode;

first signal retaining means for retaining a first electric signal outputted immediately after the integrating amplifier is switched to the accumulator mode;

second signal retaining means for retaining a second electric signal outputted from the integrating amplifier immediately before the integrating amplifier is switched to the reset mode by the switching means;

a multiplexer for switching and thereby outputting the first electric signal retained by the first signal retaining means and the second electric signal retained by the second signal retaining means respectively; and converting means for converting the first electric signal and the second electric signal outputted from the multiplexer respectively into digital signals and thereby outputting the digital signals.

7. The signal detecting device according to claim 6, wherein the charge signal is retrieved by irradiating an electromagnetic wave for retrieval from a second electrode layer side of an image detector, the image detector being formed by serially stacking a first electrode layer having transmissivity with respect to an electromagnetic wave for recording, a recording photoconductive layer which takes on conductivity by receiving irradiation of the electromagnetic wave for recording transmitted through the first electrode layer, an electric accumulator for accumulating electric charges generated in the recording photoconductive layer by irradiation of the electromagnetic wave for recording as electric charges for a latent image, a retrieving photoconductive layer which takes on conductivity by receiving irradiation of the electromagnetic wave for retrieval, and the second electrode layer having a stripe electrode composed of a plurality of line electrodes being arranged in given pitches for retrieving the electric charges for a latent image from the electric accumulator, the integrating amplifier, the first signal retaining means and the second signal retaining means are respectively provided on each of the line electrodes, and the multiplexer switches the first electric signal and the second electric signal concerning the charge signal outputted from the respective line electrodes depending on the respective line electrodes and thereby outputs the first and the second electric signals to the converting means.

8. A signal detecting device comprising:

an integrating amplifier for accumulating charge signals and for outputting electric signals corresponding to amounts of the accumulated electric charges;

switching means for switching the integrating amplifier between an accumulator mode and a reset mode;

first signal retaining means for retaining a first electric signal outputted immediately after the integrating amplifier is switched to the accumulator mode;

second signal retaining means for retaining a second electric signal outputted from the integrating amplifier immediately before the integrating amplifier is switched to the reset mode by the switching means;

first converting means for converting the first electric signal retained by the first signal retaining means into a digital signal; and second converting means for converting the second electric signal retained by the second signal retaining means into a digital signal.

9. The signal detecting device according to claim 8, wherein the charge signal is retrieved by irradiating an electromagnetic wave for retrieval from a second electrode layer side of an image detector, the image detector being formed by serially stacking a first electrode layer having transmissivity with respect to an electromagnetic wave for recording, a recording photoconductive layer which takes on conductivity by receiving irradiation of the electromagnetic wave for recording transmitted through the first electrode layer, an electric accumulator for accumulating electric charges generated in the recording photoconductive layer by irradiation of the electromagnetic wave for recording as electric charges for a latent image, a retrieving photoconductive layer which takes on conductivity by receiving irradiation of the electromagnetic wave for retrieval, and the second electrode layer having a stripe electrode composed of a plurality of line electrodes being arranged in given pitches for retrieving the electric charges for a latent image from the electric accumulator, the integrating amplifier, the first signal retaining means and the second signal retaining means are respectively provided on each of the line electrodes, the signal detecting device includes a first multiplexer for switching the first electric signal concerning the charge signal outputted from the respective line electrodes depending on the respective line electrodes and thereby outputting the first electric signal to the first converting means, and the signal detecting device includes a second multiplexer for switching the second electric signal concerning the charge signal outputted from the respective line electrodes depending on the respective line electrodes and thereby outputting the second electric signal to the second converting means.

* * * * *